(12) United States Patent
Snavely et al.

(10) Patent No.: US 6,632,638 B1
(45) Date of Patent: Oct. 14, 2003

(54) ENHANCED SOLUBILITY OF RECOMBINANT PROTEINS USING URACIL DNA GLYCOSYLASE INHIBITOR

(75) Inventors: Marshall Snavely, Moorpark, CA (US); Lana Klionsky, Ventura, CA (US)

(73) Assignee: Amgen, Inc., Thousand Oaks, CA (US)

( * ) Notice: Subject to any disclaimer, the term of this patent is extended or adjusted under 35 U.S.C. 154(b) by 194 days.

(21) Appl. No.: 09/715,521

(22) Filed: Nov. 17, 2000

(51) Int. Cl.[7] .......................... C12P 21/06; C12N 15/62; C12N 15/64; C07K 14/00
(52) U.S. Cl. .................. 435/69.1; 435/69.7; 435/71.1; 435/71.2; 536/23.1; 536/23.4; 530/350; 530/351
(58) Field of Search ................ 530/350, 351, 530/369; 435/69.1, 69.7, 71.1, 71.2; 536/234, 23.1

(56) References Cited

U.S. PATENT DOCUMENTS

| | | | |
|---|---|---|---|
| 5,322,930 A | | 6/1994 | Tarnowski et al. |
| 5,629,172 A | | 5/1997 | Mascarenhas et al. |
| 5,654,176 A | | 8/1997 | Smith |
| 6,077,689 A | * | 6/2000 | Snavely ............. 435/69.1 |

FOREIGN PATENT DOCUMENTS

| | | |
|---|---|---|
| EP | 207044 | 12/1986 |
| EP | 293249 | 11/1988 |
| WO | WO 92/13955 | 8/1992 |
| WO | WO 94/02502 | 2/1994 |
| WO | WO 94/23040 | 11/1994 |
| WO | WO 95/04076 | 2/1995 |
| WO | WO 95/16044 | 6/1995 |

OTHER PUBLICATIONS

Flaschel, et al. "Improvement of Downstream Processing of Recombinant Proteins by Means of Genetic Engineering Methods", *Biotech Adv.*, vol. 11, pp. 31–78 (1993).

Wang, et al., "Uracil–DNA Glycosylase Inhibitor Gene of Bacteriophage PBS2 Encodes a Binding Protein Specific for Uracil–DNA Glycosylase", *The Journal of Biological Chemistry*, vol. 264(2), pp. 1163–1171 (1989).

Devlin, et al., "Expression of Granulocyte Colony–Stimulating Factor by Human Cell Lines", *Journal of Leukocyte Biology*, vol. 41, pp. 302–306, (1987).

Mittl, et al., "Structure of Recombinant Human CPP32 in Complex with the Tetrapeptide Acetyl–Asp–Val–Ala–Asp Fluoromethyl Ketone", *The Journal of Biological Chemistry*, vol. 272(10), pp. 6539–6547 (1997).

Zandi, et al., "The IkB Kinase Complex (IKK) Contains Two Kinase Subunits, IKKα and IKKβ, Necessary for IkB Phosphorylation and NF–kB Activation", *Cell*, vol. 91, pp. 243–252 (1997).

Lacey, et al., "Osteoprotegerin Ligand is a Cytokine that Regulates Osteoclast Differentiation and Activiation", *Cell*, vol. 93, pp. 165–176 (1998).

Fukunaga, et al., "Functional Domains of the Granylocyte Colony–Stimulating Factor Receptor", *The EMBO Journal*, vol. 10(10), pp. 2855–2865 (1991).

Wu, et al., "The Arabidopsis 14–3–3 Multigene Family", *Plant Physiol.*, vol. 114, pp. 1421–1431 (1997).

Lu, et al., "Phosphorylation and Calcium Binding Properties of an Arabidopis GF14 Brain Protein Homolog", The Plant Cell, vol. 6, pp. 501–510, (1994).

* cited by examiner

*Primary Examiner*—Lorraine Spector
*Assistant Examiner*—Jegatheesan Seharaseyon
(74) *Attorney, Agent, or Firm*—Randolph N. Mohr; Ron K. Levy; Stuart L. Watt

(57) ABSTRACT

Disclosed are methods for improving the solubility of a protein of interest produced recombinantly by expressing the protein of interest as a fusion protein with Uracil DNA glycosylase inhibitor (UGI).

9 Claims, 9 Drawing Sheets

FIGURE 2

```
ATGaaacacc atcaccatca ccatcacACA AATTTATCTG ACATCATTGA
AAAAGAAACA GGAAAACAAC TAGTGATTCA AGAATCAATT CTAATGTTAC
CAGAAGAAGT AGAGGAAGTA ATTGGAATA  AACCAGAAAG TGATATTTTA
GTTCATACTG CTTATGATGA AAGTACAGAT GAAAATGTAA TGCTATTAAC
TTCAGATGCT CCAGAATATA AACCTTGGGC TTTAGTAATT CAAGACAGTA
ATGGAGAAAA TAAAATTAAA ATGTTAGCTA GCTAA
```

ENHANCED SOLUBILITY OF RECOMBINANT PROTEINS USING URACIL DNA GLYCOSYLASE INHIBITOR

FIELD OF THE INVENTION

This invention relates to methods of increasing the solubility of proteins produced recombinantly. Specifically, the invention is directed to production of recombinant proteins as fusion proteins in order to increase their solubility.

BACKGROUND OF THE INVENTION

Advances in molecular biology and the exploitation of recombinant DNA procedures has made possible the production of significant quantities of foreign proteins in certain host cell systems. Recombinant proteins are produced in the host cell systems by transfecting the host cells with DNA coding for the protein of interest, and then growing the transfected host cells under conditions that allow for expression of the new recombinant protein.

Prokaryotic cells have become the system of choice for expression of cloned genes encoding eukaryotic and prokaryotic polypeptides, and numerous expression systems exist for expression of gene products in bacteria. The expression of genes in *E. coli* has become established as a key technique in the understanding of molecular processes and *E. coli* expression systems have become a standard and popular method for the production and large-scale purification of exogenous proteins. Importantly, the technology has provided a source of proteins in a quantity and quality that was previously difficult, or impossible, to achieve through isolation from natural sources.

When recombinant proteins are expressed in *E. coli*, they frequently form insoluble protein aggregate complexes commonly referred to as "inclusion bodies". Recovery of the desired protein which is in the form of such inclusion bodies has presented a number of problems. For example, it can be difficult to isolate the inclusion bodies from other host cellular materials, and to subsequently remove inclusion body protein contaminants from the desired inclusion body protein. Additionally, the inclusion body protein is often in the form which, while identifiable as the desired protein, is not biologically active. In such instances, denaturants and detergents (e.g., guanidine hydrochloride, urea, sodium dodecylsulfate (SDS), Triton X-100) have to be used to extract the protein. The resultant solution containing the denatured protein with the individual polypeptide chains unfolded is then treated to remove the denaturant or otherwise reverse the denaturing conditions and thereby permit renaturation of the protein and "folding" of the polypeptide chains in solution to yield protein in native, biologically active form.

One strategy for avoiding the problems with refolding would be to facilitate the proper folding of recombinant protein within the cell, thus preventing the formation of inclusion bodies. The problem is that the folding processes can be quite slow and involve reactive intermediates which aggregate and compete with the slower process of folding into the native conformation. Inhibition of the competing aggregation pathway would facilitate proper folding of recombinantly expressed proteins. One way to inhibit aggregation is to enhance the solubility of recombinantly produced proteins of interest by preparing the protein of interest as a "fusion protein", i.e., fuse the protein of interest to another protein that folds readily into a highly stable conformation.

To prepare a fusion protein (also known as a "chimeric protein"), the gene encoding the protein of interest can be attached to a second gene encoding a second protein, termed a "fusion partner". In this way, a single polypeptide is produced by the host cell, and the polypeptide is comprised of the protein of interest and the fusion partner. The fusion partner may be homologous (i.e., from the same species and/or strain as the host cell) or heterologous (i.e., from a species and/or strain other than that of the host cell) to the host cell. Examples of commonly used fusion partners include, inter alia, maltose binding protein ("MBP"), glutathione-s-transferase ("GST"), hexaHistidine ("hexaHis") the lacZ and trpE gene products, ubiquitin, and thioredoxin. While each of these fusion partners has been demonstrated to enhance the solubility of at least one protein of interest, certain other proteins of interest do not demonstrate enhanced solubility when linked to these fusion proteins.

In certain cases, particularly where it is desirable to obtain the protein of interest in a purified form, the fusion partner and protein of interest must be separated from each other after synthesis as a single polypeptide. One means to achieve this is to provide a peptide linker between the fusion partners. This is accomplished by adding nucleic acid sequence encoding the peptide between the gene encoding the protein of interest and the gene encoding the fusion partner. Typically, this "linker sequence" DNA encodes an oligopeptide that contains a "cleavage recognition sequence" for an endopeptidase such as enterokinase, Factor Xa, caspase, or thrombin. The endopeptidase, when presented with a fusion protein containing its specific target sequence, can thus cleave the fusion protein into its two components.

For further discussions of fusion proteins see, for example, WO 95/04076, published Feb. 9, 1995; U.S. Pat. No. 5,629,172 issued May 13, 1997; WO 94/23040, published Oct. 13, 1994; Flaschel et al., *Biotech Adv.*, 11:31–78 (1993); European patent application 207,044, published Dec. 30, 1986; U.S. Pat. No. 5,322,930, issued Jun. 21, 1994; European Patent 293,249, published Nov. 30, 1988; U.S. Pat. No. 5,654,176, issued Aug. 5, 1997; WO 95/16044, published Jun. 15, 1995; WO 94/02502, published Feb. 3, 1994; and WO 92/13955, published Aug. 20, 1992.

Uracil DNA glycosylase inhibitor (UGI) is a heat stable, acidic, low molecular weight protein expressed from the *Bacillus subtilis* phage, PBS1 or PBS2. The function of UGI is to inhibit the repair system that removes uracil from DNA and replaces it with thymine, allowing the phage to use uracil exclusively in its DNA. UGI has a molecular weight of 9.5 kD, a pI of 3.96, is stable to boiling, and is well-expressed in *E. coli*.

It is an object of the present invention to provide new methods of enhancing the solubility of recombinant proteins produced in bacterial host cells, through utilization of UGI as a fusion partner.

SUMMARY OF THE INVENTION

In one embodiment, the present invention provides a method of increasing the solubility of a protein of interest produced in a host cell comprising expression of the protein as a fusion protein with UGI. Optionally, the protein of interest is selected from the group consisting of: extracellular domains of membrane-bound receptor proteins, cytokines and cytokine-like proteins, the catalytic domain of serine/threonine kinases, and members of the TNF family. Additionally, the host cell may be a prokaryotic cell such as a bacterial cell, and the bacterial cell may be an *E. coli* cell.

In yet another embodiment, the invention provides a method of increasing the solubility of a protein of interest produced in a host cell comprising expressing the protein as a fusion protein with UGI, wherein the fusion protein contains a linker peptide.

BRIEF DESCRIPTION OF THE DRAWINGS

FIG. 2 (SEQ ID NO:1) depicts the sequence of a full length synthetic UGI gene of the present invention. The nucleotide sequence corresponds to the full length sense strand of UGI from the B. subtilus bacteriophage, PBS2. A 24 base sequence was inserted at the 5' end of the gene to add a lysine residue and a seven-histidine tag (shown in lower case). A 6 base insertion at the 3' end added a restriction site in front of the stop codon. Nucleotides were altered to introduce convenient restriction sites within the gene and to optimize codons for expression in E. coli. The codons changes did not result in changes in the amino acid sequence.

DETAILED DESCRIPTION OF THE INVENTION

Figure 1:
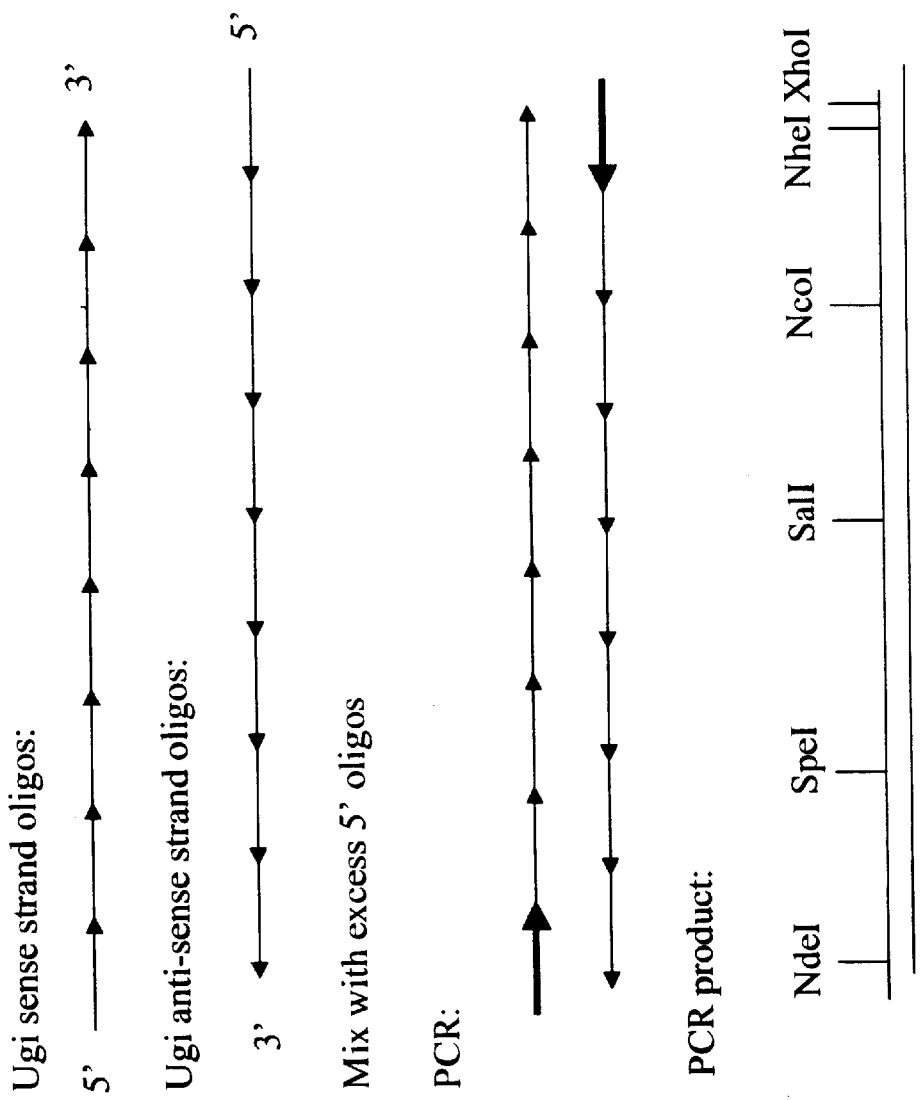
FIG. 1 is a diagram of the strategy used to prepare a synthetic full length UGI gene.

This invention is based on the unexpected discovery that the solubility of a protein of interest, when produced in a bacterial host cell, can be increased by expressing the protein as a fusion protein with UGI.

The term "fusion protein" refers to two polypeptides or fragments of polypeptides (also called "fusion partners") which are synthesized in host cells from a nucleic acid molecule encoding both polypeptides (and optionally encoding a linker peptide as well) or fragments thereof. For purposes herein, one polypeptide of the fusion protein is UGI or fragment thereof, and the other polypeptide is a "protein of interest" or fragment thereof. The fusion protein may have the UGI polypeptide situated at the amino terminus of the protein of interest or situated at the carboxyl terminus of the protein of interest. Optionally, the fusion protein may contain a "linker peptide" situated between the two fusion partners. The DNA construct encoding the fusion protein partners is referred to as the "fusion protein DNA" or the "fusion protein DNA construct".

The terms "protein of interest" and "polypeptide of interest" refer to a polypeptide produced recombinantly in a host cell as one member of a fusion protein. The polypeptide of interest may be homologous or heterologous to the host cell, and may be a naturally occurring polypeptide, or a substitution, deletion, and/or insertion variant of a naturally occurring polypeptide. Further, the polypeptide may be a full length molecule or a truncated version of the full length molecule. The polypeptide of interest may or may not have an amino terminal methionine. Optionally, the polypeptide of interest may itself be a fusion or chimeric polypeptide, such as, for example, where the Fc portion of an antibody is fused to the polypeptide of interest, where an affinity tag (such as hexaHis) is fused to the polypeptide of interest, and the like. Preferred polypeptides of interest include extracellular domains of receptor proteins, cytokines and cytokine-like proteins, kinase domains of serine/threonine kinases, and members of the TNF family.

UGI contemplated for use in the present invention will have the amino acid sequence of the synthetic UGI set forth in FIG. 2 (SEQ ID NO:1). The nucleotides encoding the amino acid sequence of UGI are nucleotides 28–276 of FIG. 2.

The term "linker peptide" refers to a peptide located between the two fusion partner polypeptides in a fusion protein construct. The linker peptide will generally consist of at least five to ten amino acids, but may optionally be longer or shorter. Typically, the amino acids will be chosen from the group of thr, ser, pro, asp, gly, lys, gln, asn, and ala, which are prevalent in naturally occurring linkers located between independently folding domains of proteins (see Argos, *J. Mol. Biol.* 211:943–958 [1990]). The amino acid sequence of the linker peptide may be a naturally occurring sequence or a synthetic sequence. Optionally, the linker peptide will have an endoproteinase site, such that the UGI portion of the fusion protein can be separated from the protein of interest after the fusion protein has been generated.

A DNA molecule encoding the full length protein of interest or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, *Current Protocols in Molecular Biology*, Green Publishers Inc. and Wiley and Sons, NY (1994). A gene or cDNA encoding the protein of interest or fragment thereof may be obtained for example by screening a genomic or cDNA library with a suitable probe. Suitable probes include, for example, oligonucleotides, cDNA fragments, or genomic DNA fragments, that are expected to have some homology to the gene encoding the protein of interest, such that the probe will hybridize with the gene encoding the protein of interest under selected hybridization conditions. An alternate means of screening a DNA library is by polymerase chain reaction "PCR" amplification of the gene encoding the protein of interest. PCR is typically accomplished using oligonucleotide "primers" which have a sequence that is believed to have sufficient homology to the gene to be amplified such that at least a sufficient portion of the primer will hybridize with the gene.

If the library to be screened is an expression library, an antibody which is believed to recognize and bind an epitope of the protein of interest can be used as a screening tool.

Alternatively, a gene encoding the protein of interest or fragment thereof may be prepared by chemical synthesis using methods well known to the skilled artisan such as those described by Engels et al., *Angew. Chem. Intl. Ed.*, 28:716–734 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the protein of interest will be several hundred nucleotides in length. Nucleic acids larger than about 100 nucleotides can be synthesized as several fragments using these methods. The fragments can then be ligated together to form a gene coding for the full length protein of interest. Usually, the DNA fragment encoding the amino terminus of the polypeptide will have an ATG, which encodes a methionine residue. This methionine may or may not be present on the mature form of the protein of interest. The methionine can be removed inside the cell or during the process of secretion.

In some cases, it may be desirable to prepare nucleic acid and/or amino acid variants of the naturally occurring protein of interest. Nucleic acid variants (wherein one or more nucleotides are designed to differ from the wild-type or naturally-occurring protein of interest) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions that add or remove recognition sites for restriction endonucleases or that account for codon preference in bacterial host cells. Other preferred variants are those encoding conservative amino acid changes. (e.g., wherein the charge or polarity of the naturally occurring amino acid side chain is not altered substantially by substitution with a different amino acid) as compared to wild type.

A DNA molecule encoding a UGI polypeptide can be prepared using the methods described above for preparation of the gene encoding the protein of interest. Preferred variants of UGI polypeptides include UGI with the nucleic acid sequence altered to optimize expression in *E. coli* and to introduce convenient restriction sites. A general discussion of codon optimization for expression in *E. coli* is described in Kane, *Curr. Opin. Biotechnol.*, 6:494–500 (1995).

Once the genes encoding the protein of interest and the UGI polypeptide have been obtained, they may be modified using standard methods to create restriction endonuclease sites at the 5' and/or 3' ends. Creation of the restriction sites permits the genes to be properly inserted into amplification and/or expression vectors. Addition of restriction sites is typically accomplished using PCR, where one primer of each PCR reaction typically contains, inter alia, the nucleotide sequence of the desired restriction site.

There are several ways to prepare the DNA construct encoding the fusion protein which comprises the UGI gene, the gene encoding the protein of interest, and, optionally, a DNA molecule encoding a linker peptide which is located between the two genes.

In one procedure, the UGI gene and gene encoding the protein of interest (the "fusion partner genes") can be ligated together in either orientation (e.g., UGI gene at the 5' or 3' end of the construct). Where a linker DNA molecule is to be included, it can first be ligated to one of the fusion partner genes, and that construct can then be ligated to the other fusion partner gene. Ligations are typically accomplished using DNA ligase enzyme in accordance with the manufacturer's instructions.

A separate procedure provides for first ligating one fusion partner gene into the selected vector, after which the other fusion partner gene can be ligated into the vector in a position that is either 3' or 5' to the first fusion partner gene. Where a linker DNA molecule is to be included, the linker DNA molecule may be ligated to either fusion partner gene either before or after that gene has been ligated into the vector.

The gene or cDNA encoding the protein of interest or fragment thereof can be inserted into an appropriate expression vector for expression in a host cell. The vector is selected to be functional in the particular host cell employed (i.e., the vector is compatible with the host cell machinery such that amplification and/or expression of the gene encoding the protein of interest can occur).

Typically, the vectors used in any of the host cells will contain a promoter (also referred to as a "5' flanking sequence") and other regulatory elements as well such as an enhancer(s), an origin of replication element, a transcriptional termination element, a ribosome binding site element, a polylinker region for inserting the nucleic acid encoding the polypeptide to be expressed, and a selectable marker element. Each of these elements is discussed below. Optionally, the vector may contain a "tag" DNA sequence, i.e., an oligonucleotide sequence located at either the 5' or 3' end of the fusion DNA construct. The tag DNA encodes a molecule such as hexaHis, c-myc, FLAG (Invitrogen, San Diego, Calif.) or another small immunogenic sequence. When placed in the proper reading frame, this tag will be expressed along with the fusion protein, and can serve as an affinity tag for purification of the fusion protein from the host cell. Optionally, the tag can subsequently be removed from the purified fusion protein by various means such as using a selected peptidase for example.

The promoter may be homologous (i.e., from the same species and/or strain as the host cell), heterologous (i.e., from a species other than the host cell species or strain), hybrid (i.e., a combination of promoters from more than one source), synthetic, or it may be the native protein of interest promoter. Further, the promoter may be a constitutive or an inducible promoter. As such, the source of the promoter may be any unicellular prokaryotic or eukaryotic organism, any vertebrate or invertebrate organism, or any plant, provided that the promoter is functional in, and can be activated by, the host cell machinery.

The promoters useful in the vectors of this invention may be obtained by any of several methods well known in the art. Typically, promoters useful herein will have been previously identified by mapping and/or by restriction endonuclease digestion and can thus be isolated from the proper tissue source using the appropriate restriction endonucleases. In some cases, the full nucleotide sequence of the promoter may be known. Here, the promoter may be synthesized using the methods described above for nucleic acid synthesis or cloning.

Where all or only a portion of the promoter sequence is known, the complete promoter may be obtained using PCR and/or by screening a genomic library with suitable oligonucleotide and/or 5' flanking sequence fragments from the same or another species.

Suitable promoters for practicing this invention are inducible promoters such as the lux promoter, the lac promoter, the arabinose promoter, the trp promoter, the tac promoter, the tna promoter, synthetic lambda promoters (from bacteriophage lambda), and the T5 or T7 promoters. Preferred promoters include the lux, and lac promoters.

The origin of replication element is typically a part of prokaryotic expression vectors whether purchased commercially or constructed by the user. In some cases, amplification of the vector to a certain copy number can be important for optimal expression of the protein or polypeptide of interest. In other cases, a constant copy number is preferred. In any case, a vector with an origin of replication that fulfills the requirements can be readily selected by the skilled artisan. If the vector of choice does not contain an origin of replication site, one may be chemically synthesized based on a known sequence, and ligated into the vector.

The transcription termination element is typically located 3' of the end of the fusion protein DNA construct, and serves to terminate transcription of the RNA message coding for the fusion polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

Expression vectors typically contain a gene coding for a selectable marker. This gene encodes a protein necessary for the survival and growth of a host cell grown in a selective culture medium. Typical selection marker genes encode proteins that (a) confer resistance to antibiotics or other toxins, e.g., ampicillin, tetracycline, chloramphenicol, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, the chloramphenicol resistance gene, and the tetracycline resistance gene.

The ribosome binding element, commonly called the Shine-Dalgarno sequence in prokaryotes, is necessary for the initiation of translation of mRNA. The element is typically located 3' to the promoter and 5' to the coding sequence of the fusion protein DNA construct. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

Each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting can be accomplished by first filling in "sticky ends" using an enzyme such as Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

Another method for constructing the vector is to conduct all ligations of the various elements simultaneously in one reaction mixture. Here, many nonsense or nonfunctional vectors may be generated due to improper ligation or insertion of the elements, however the functional vector may be identified by expression of the selectable marker. Proper sequence of the ligation product can be confirmed by digestion with restriction endonucleases or by DNA sequencing.

After the vector has been constructed and a fusion protein DNA construct has been inserted into the proper site of the vector, the completed vector may be inserted into a suitable host cell for fusion protein expression.

Host cells suitable for the present invention are bacterial cells. For example, the various strains of *E. coli* (e.g., HB101, JM109, DH5α, DH10, and MC1061) are well-known host cells for use in preparing recombinant polypeptides. The choice of bacterial strain is typically made so that the strain and the expression vector to be used are compatible. Various strains of *B. subtilis*, Pseudomonas spp., other Bacillus spp., Streptomyces spp., and the like may also be employed in practicing this invention in conjunction with appropriate expression vectors.

Insertion (also referred to as "transformation" or "transfection") of the vector into the selected host cell may be accomplished using such methods as calcium phosphate precipitation or electroporation. The method selected will in part be a function of the type of host cell to be used. These methods and other suitable methods are well known to the skilled artisan, and are set forth, for example, in Sambrook et al., supra.

The host cells containing the vector (i.e., transformed or transfected host cells) may be cultured using one or more standard media well known to the skilled artisan. The selected medium will typically contain all nutrients necessary for the growth and survival of the host cells. Suitable media for culturing *E. coli* cells, are, for example, Luria broth ("LB"), YT broth, SOB, SOC, and/or Terrific Broth ("TB").

Typically, the antibiotic or other compound useful for selective growth of the transformed cells is added as a supplement to the medium. The compound to be used will be determined by the selectable marker element present on the plasmid with which the host cell was transformed. For example, where the selectable element confers kanamycin resistance, the compound added to the culture medium will be kanamycin.

Host cells with vectors containing fusion protein DNA constructs under the control of constitutive promoters are capable of continuous fusion protein production throughout the host cell culture period. However, host cells with vectors containing fusion protein DNA constructs under the control of inducible promoters generally do not produce significant amounts of fusion protein unless the promoter is "turned on" by exposing the host cells to the proper temperature (for temperature inducible promoters) or chemical compound(s). For example, where the fusion protein DNA construct is under the control of the lac promoter, the compound IPTG (isopropyl β-D-thiogalactopyranoside) is typically added to the host cell culture medium to induce high-level protein production.

The solubility of the fusion protein, or of the protein of interest after it has been cleaved from the fusion partner, can be determined using standard methods known in the art. Typically, host cells are collected three to four hours after induction and the cells are lysed. Cell lysis may be accomplished using physical methods such as homogenization, sonication, French press, microfluidizer, or the like, or by using chemical methods such as treatment of the cells with EDTA and a detergent; Falconer et al., *Biotechnol. Bioengin.*, 53:453–458 (1997). In some cases, it may be advantageous to use both chemical and physical means.

Separation of soluble and insoluble material is typically accomplished by centrifugation at around 18,000×g for about 20 minutes. After the soluble and insoluble materials have been separated, visualization of soluble and insoluble fusion protein can be readily accomplished using denaturing gel electrophoresis. With this technique, equivalent volumes of soluble and insoluble fractions are applied to the gel, and the amount of fusion protein (or protein of interest and/or UGI polypeptide if the two have been previously separated by cleavage; see below) can be detected by staining the gel or by Western blot, provided an antibody specific for the fusion protein, the protein of interest, or the UGI polypeptide (depending on which entity is being assessed), or other appropriate Western blot "detection tool" is available.

Purification of the fusion protein or the protein of interest (if the cleavage step has already been conducted) from solution can be accomplished using a variety of techniques. If the polypeptide has been synthesized such that it contains a tag such as Hexahistidine ("hexaHis") or other small peptide such as myc or FLAG, for example, at either its carboxyl or amino terminus, it may essentially be purified in a one-step process by passing the solution over an affinity column where the column matrix has a high affinity for the tag or for the polypeptide directly (i.e., an antibody specifically recognizing the protein of interest). For example, polyhistidine binds with great affinity and specificity to nickel, thus an affinity column containing nickel (such as the Qiagen nickel columns) can be used for purification of the protein of interest/hexaHis; Ausubel et al., eds., *Current Protocols in Molecular Biology*, Section 10.11.8, John Wiley & Sons, New York (1993).

Where the fusion protein and/or the protein of interest has no tag and no antibodies are available, purification may be accomplished using standard methods such as those set forth below and in Marston et al., *Meth. Enz.*, 182:264–275 (1990). Such procedures include, without limitation, ion exchange chromatography, hydroxyapatite chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

The present invention is useful for enhancing direct expression of recombinantly produced polypeptides, as inclusion body formation is decreased or prevented, and solubility of the polypeptide of interest is increased.

In some cases, the polypeptide of interest may not be biologically active when expressed as a fusion protein with a UGI polypeptide. One reason for this may be lack of folding or improper folding of the polypeptide by the host cell machinery. To enhance the proper folding of the polypeptide of interest, the host cells expressing the fusion construct containing the polypeptide of interest may also be transformed with individual chaperone proteins and/or groups of chaperone proteins that are known to facilitate proper folding. The novelty of this approach is that fusion to UGI protein prevents inclusion body formation, allowing the molecular chaperones more time in which to interact with a slowly-folding, rapidly-produced, aggregation-prone protein of interest. Here, the fusion protein containing the polypeptide of interest will be co-expressed with one or more chaperone proteins, leading to enhanced folding and increased biological activity of the protein of interest.

Examples of chaperone proteins that may be suitable for this use include, without limitation, members of the HSP 70 (heat shock protein 70) family and their cohorts such as the DNAK and DNAJ proteins (which are native to *E. coli*), members of the HSP 60 family of proteins and their cohorts such as GROEL and GROES proteins (also native to *E. coli*), and members of the family of small heat shock proteins such as the protein SEC-1 from *C. elegans*.

The following Examples are intended for illustration purposes only, and should not be construed to limit the invention in any way.

EXAMPLE 1

This example describes the preparation of the uracil-DNA glycosylase inhibitor (UGI) DNA used to prepare the fusions of the present invention.

The DNA and amino acid sequences of the uracil-DNA glycosylase inhibitor (UGI) are known (see Wang and Mosbaugh, *J. Biol. Chem.*, 264:1163–1171 [1989]). These sequences have been deposited in Genbank as accession number J04434.

Synthetic UGI DNA was prepared based on the sequence of a clone from the *B. subtilus* bacteriophage, PBS2. Nucleotides were altered to introduce convenient restriction sites and to optimize codons for expression in *E. coli*. The codons changes did not result in changes in the amino acid sequence.

The strategy for preparing the synthetic UGI gene may be best understood by referring to the diagram in FIG. 1. The restriction site additions are indicated in the Figure. Eight oligonucleotides of about 40 bases each were synthesized using the phosphoramidite method for oligonucleotide synthesis. These oligonucleotides, when aligned 5' to 3', correspond to the full length sense strand of UGI from PBS2 with a 40 base extension at the 5' end of the gene, a 28 base extension at the 3' end, and the nucleotide changes mentioned above. The 5' extension added a restriction site and a seven-histidine tag. The 3' extension added a restriction site and a termination codon. The sequence of each of the eight oligonucleotides is set forth below:

ACAAACACCACATATGAAACACCATCAC-CATCACCAT (SEQ ID NO:2)

CACACAAATTTATCTGACATCAT-TGAAAAAGAAACAGGAA (SEQ ID NO:3)

AACAACTAGTGATTCAAGAATCAAT-TCTAATGTTACCAGA (SEQ ID NO:4)

AGAAGTAGAGGAAGTAATTGG-GAATAAACCAGAAAGTGAT (SEQ ID NO:5)

ATTTTAGTTCATACTGCTTATGAT-GAGTCGACAGATGAAA (SEQ ID NO:6)

ATGTAATGCTATTAACTTCAGATGCTC-CAGAATATAAACC (SEQ ID NO:7)

ATGGGCTTTAGTAATTCAAGACAG-TAATGGAGAAAATAAA (SEQ ID NO:8)

ATTAAAATGTTAGGTAGTGGTACTGGCG-GTGCTAGCTAAT (SEQ ID NO:9)

Separately, eight different oligonucleotides were prepared; these eight oligonucleotides of about 40 bases each, when aligned 5' to 3', correspond to the full length antisense strand of UGI from PBS2 with a 43 base extension on the 5' end, a 23 base extension on the 3' end, and the nucleotide changes mentioned above. The 5' extension added restriction sites and a termination codon. The 3' extension added a seven-histidine tag. The sequence of each of these eight oligonucleotides is set forth below:

CACCCAACCCTCGAGATTAGCTAGCAC-CGCCAGTA (SEQ ID NO:10)

CCACTACCTAACATTTTAATTT-TATTTTCTCCATTACTGT (SEQ ID NO:11)

CTTGAATTACTAAAGCCCATGGTT-TATATTCTGGAGCATC (SEQ ID NO:12)

TGAAGTTAATAGCATTACATTTTCATCT-GTCGACTCATCA (SEQ ID NO:13)

TAAGCAGTATGAACTAAAATAT-CACTTTCTGGTTTATTCC (SEQ ID NO:14)

CAATTACTTCCTCTACTTCTTCTGGTAA-CATTAGAATTGA (SEQ ID NO:15)

TTCTTGAATCACTAGTTGTTTTCCT-GTTTCTTTTTCAATG (SEQ ID NO:16)

ATGTCAGATAAATTTGTGTGATGGT-GATGGTGATGGTGTT (SEQ ID NO:17)

To prepare double-stranded UGI DNA, about one pmol each of oligonucleotides SEQ ID NOS:3 through 9 and SEQ ID NOS:11 through 17 were placed into a small tube together with about 10 pmol each of oligonucleotides SEQ ID NO:2 and SEQ ID NO:10. To this mixture was added PCR buffer, about 0.2 mM dNTP and about 25 U of Taq polymerase (Boehringer Mannheim) in a final volume of 500 µl. The reaction mix was split into five tubes and polymerase chain reaction (PCR) was carried out. Forty cycles were conducted with the following parameters: 94° C. for 30 seconds, 42° C. for 30 seconds, and 72° C. for 30 seconds. After PCR, a small aliquot of reaction product was run on an agarose gel to confirm that the PCR product was the correct size. The remaining PCR product from all five tubes was precipitated with ethanol and resuspended in 100 µl of H$_2$O. One half µl of the first round product was used as template in a second round of PCR to further amplify the product. The second reaction mixture contained, in addition to template, PCR buffer, 0.2 mM DNTP, about 20 pmol each of oligonucleotides SEQ ID NO:2 and SEQ ID NO:10, and about 5 U of Taq polymerase in a final volume of about 100 µl. DNTP and polymerase were from Boehringer Mannheim. Forty cycles of PCR were conducted using the following parameters: 94° C. for 30 seconds, 50° C. for 30 seconds, and 72° C. for 30 seconds.

Product from the second round of PCR was digested with NdeI and XhoI following the manufacturer's protocol (New England Biolabs). The digested fragment was precipitated with ethanol, resuspended in H$_2$O, and ligated into pAMG33 (ATCC Accession No. 207082) digested with the same enzymes and purified from an agarose gel. The ligation was conducted in a volume of about 10 µl containing about 1 mM ATP, 1 U of T4 DNA ligase (Boehringer Mannheim), about 20 ng of vector, 0.5–2.0 ng of insert, and ligase buffer (Boehringer Mannheim). The reaction was incubated overnight at about 14° C., ethanol precipitated, resuspended in 5 µl of H$_2$O. The resulting solution of DNA was used to transform about 50 µl of competent *E. coli* GM221 cells (ATCC Accession No. 202077) by electroporation with a Biorad GenePulser (Biorad Laboratories, Hercules, Calif.) using 2.5 V, 25 UFD, and 200 ohms in a cuvette with a gap length of about 2 mm.

After electroporation, the cells were allowed to recover in about 5 ml of Luria broth for about one hour at 30° C. The entire transformation mix was plated on Luria broth agar containing 40 μg/ml kanamycin. Colonies were screened for presence of the UGI clone by PCR using oligonucleotides directed against flanking vector sequence. Colonies were picked directly into a PCR reaction mix containing about 4 pmol of each primer, about 0.2 mM dNTP, about 1 U Taq polymerase, and PCR buffer (Boehringer Mannheim) in a final volume of about 20 μl. The PCR cycle parameters used were: 94° C. for 30 seconds, 42° C. for 30 seconds, and 72° C. for 30 seconds for a total of 40 cycles. The PCR products were evaluated by agarose gel electrophoresis.

Six clones yielding a fragment of the expected size (about 500 bp) were selected for DNA sequencing. Mutations were found in the 5' end of coding region of all six clones. A single clone with a deletion near the 5' end of the coding region, causing a frame shift, was chosen for repair of the mutation by PCR. To avoid synthesis of a very long 5'oligonucleotide, the repair was done in two steps using two different 5' PCR oligonucleotides (SEQ ID NOS:18 and SEQ ID NO:19) to generate product. At the same time, a 3' oligonucleotide (SEQ ID NO:20) was designed to remove the linker region in the original construct. The oligonucleotides used were:

TCACCATCACCACACAAATTTATCTGACATCATTG (SEQ ID NO:18)

CAAACACCACATATGAAACACCATCAT-CACCATCACCACAC (SEQ ID NO:19)

CACCCAAACCTCGAGTTAGCTAGCTAA-CATTTTAATTTTATTTTCTC (SEQ ID NO:20)

The PCR reaction to alter the mutant UGI clone was performed in two stages. In the first step, the mutant clone was used as template in a reaction of about 100 μl containing 10 pmol each of SEQ ID NO:18 oligonucleotide and SEQ ID NO:20 oligonucleotide, and other components as described above. After 30 cycles using the parameters described for generation of the original clones, an aliquot of the reaction was analyzed for size and yield of product on an agarose gel. The product of this PCR reaction was used as template in an identical reaction except that SEQ ID NO:19 oligonucleotide was used in place of SEQ ID NO:18 and the annealing temperature of the PCR method was 45° C. After checking size and yield on an agarose gel, the product was digested with NdeI and XhoI following the manufacturer's instructions (New England Biolabs). The PCR product was ligated with the expression vector, pAMG21 (see PCT WO 97/23614, published Jul. 3, 1997 for a description of pAMG21), digested the same way except that the vector was treated with about 1 U of calf intestinal phosphatase for 30 minutes at about 37° C. following digestion to prevent recircularization during ligation. The ligation reaction contained about 30 ng of dephosphorylated vector purified from an agarose gel, 4–8 ng of insert, about 1 mM ATP, about 2 U of T4 DNA ligase, and ligase buffer (Boehringer Mannheim) in a volume of about 10 μl. The reaction was incubated overnight at about 14° C. and the ethanol-precipitated DNA was used to transform E. coli cells as described above.

Colonies were screened by PCR as described above using oligonucleotides specific for the vector. Two clones that were judged to contain the insert were subjected to DNA sequencing. Both clones were identical and coded for the UGI polypeptide with methionine, lysine, and seven histidines fused to the N-terminus. The nucleotide and amino acid sequences of synthetic UGI are shown in FIG. 2.

To express the UGI polypeptide from the UGI DNA inserted into the pAMG21 vector, a 5 ml culture was prepared in Luria broth containing about 40 μg/ml kanamycin. The culture was incubated for several hours in an air shaker at 30° C. About 100 μl of this culture were then used to inoculate 50 ml of Luria broth containing about 40 μg/ml kanamycin in a 250 ml shaker flask. The cells were grown on the bench overnight with shaking. The following day, the culture was placed in a shaking incubator at 30° C. and grown to an optical density at 600 nm of about 0.7 (spectrophotometer model no. DU640, Beckman Instruments, Fullerton, Calif.), after which a pre-induction sample was taken and autoinducer (N-beta-ketocaproyl-DL-homoserinelactone, K3255, Sigma) was added to about 30 ng/ml to induce production of the UGI polypeptide.

Figure 3:
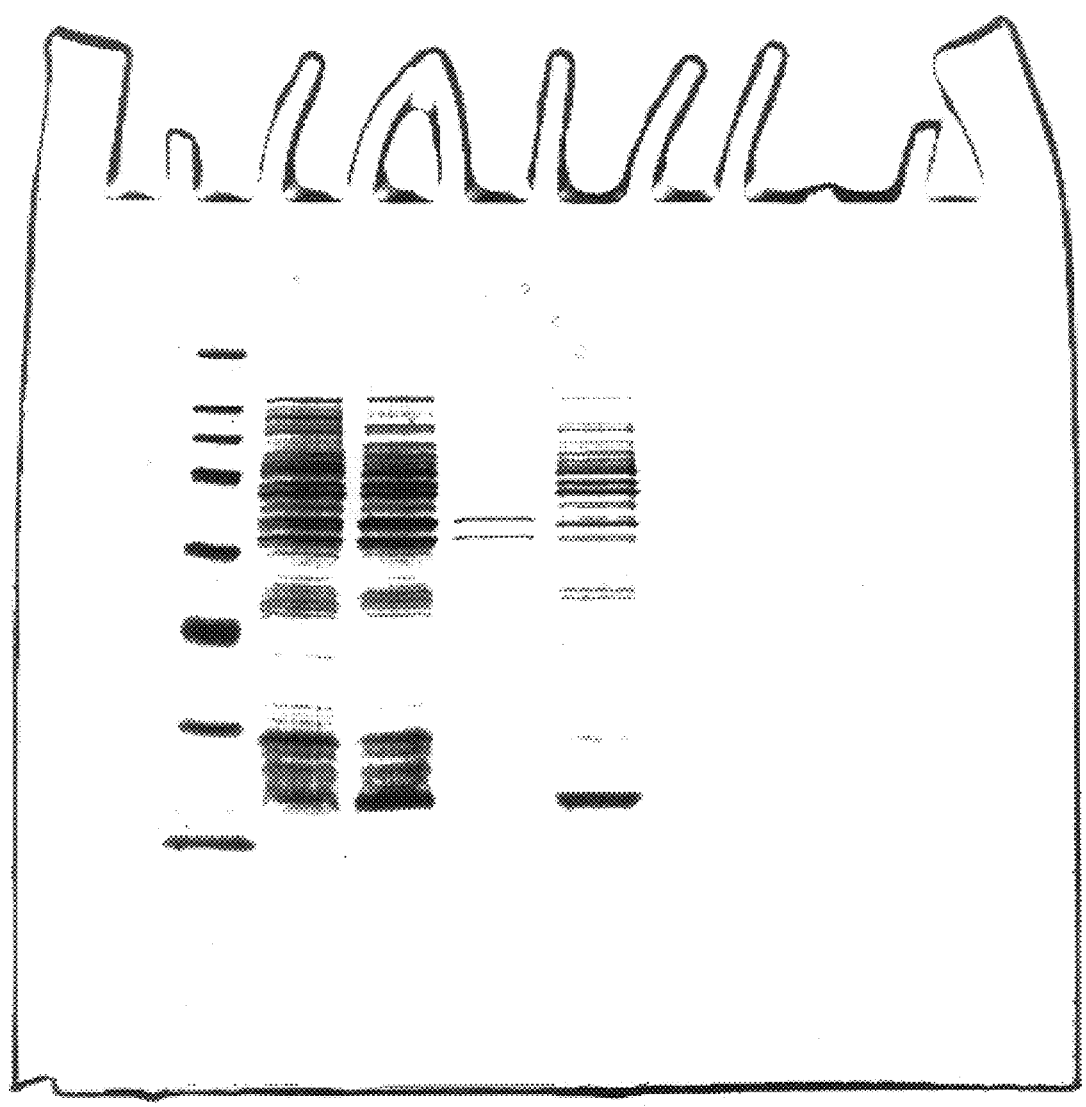
FIG. 3 is a SDS gel which demonstrates that a particular UGI protein, his-UGI, is found primarily in the soluble fraction when produced in E. coli. Lane 1 is a molecular weight marker. Lane 2 is a pre-induction sample. Lane 3 is the whole cell lysate after induction. Lane 4 is a post-induction, post-centrifugation insoluble fraction and Lane 5 is a post-induction, post-centrifugation soluble fraction. Equal amounts of insoluble and soluble fractions were analyzed.

After about 4 hours shaking at 30° C., a post-induction sample was taken, the cells were pelleted, and were resuspended in 10 ml of a buffer solution containing 10M Tris-HCL, pH 8.0 and 1 mM EDTA ("TE" buffer). The cells were then broken using a microfluidizer (M-110S, Microfluidics, Newton, Mass.) at an input pressure of about 90 psi and the solution was centrifuged at about 18,000×g for about 20 minutes to pellet insoluble material. After centrifugation, the supernatant was removed and the pellet was resuspended in an equal volume of TE. Equal amounts supernatant and pellet fractions were analyzed by SDS-PAGE. This gel is shown in FIG. 3. As can be seen, a band of about 10 kDa was observed primarily in the soluble fraction (Lane 5). Thus, his-UGI is soluble when expressed in E. coli.

In order to minimize potential toxicity due to preinduction leakage, a vector containing UGI preceded by an MS2 site was constructed. Expression vector systems utilizing MS2 coat protein and MS2 sites are described in PCT WO 99/38985. An oligonucleotide (SEQ ID NO:21) was designed to add an MS2 site to the 5' end of the UGI coding region by PCR. oligonucleotide SEQ ID NO:20, described above, was used to add a XhoI restriction site following a stop codon to the 3'end.

CACCCAACCTCTAGAAAACATGAGGAT-CACCCATGACAAATTTATCTGACATC (SEQ ID NO:21)

The UGI clone constructed previously was used as template in a PCR reaction with oligonucleotides SEQ ID NO:20 and SEQ ID NO:21 as primers. Reaction conditions were similar to those described above. PCR product was precipitated with ethanol, resuspended in water, and digested with XbaI and XhoI (New England Biolabs) following the manufacturer's protocol. Expression vector pAMG21 was digested in the same manner and then treated with calf intestinal phosphatase. The vector and insert were purified from an agarose gel, ethanol precipitated, and mixed in a 20 μl ligation reaction containing about 1 mM ATP, 2U of T4 DNA ligase, and ligase buffer. Ligation reaction was incubated overnight at 16° C., precipitated with ethanol and transformed into E.coli GM221 cells by electroporation as described previously. Colonies obtained by this procedure were screened by PCR for the presence of an appropriately sized insert using oligonucleotides directed against flanking vector sequence. DNA sequencing of a clone that was positive by PCR confirmed the presence of an MS2 site added to the 5' end of the UGI coding region.

EXAMPLE 2

This example describes the preparation of a UGI/GCSF fusion.

A DNA construct for fusing GCSF to a number of different fusion partners was created by PCR. DNA encoding the mature, human GCSF; Devlin et al., *J Leukoc. Biol.*, 41:302–306 (1987) was used as a template in a two-step process. The first PCR reaction was designed to add DNA encoding a cleavage site for the caspase 3 protease (DEVD, SEQ ID NO:22) to the 5' end of the region coding for GCSF and an XhoI restriction site following a stop codon to the 3' end. The following oligonucleotides were used in a PCR reaction similar to those described above:

GGCGGTGACGAAGTTGACACTCCATTAG-GTCCTGC (SEQ ID NO:23)

CACCCACTCGAGATTACGGCTGAGCCAGATG (SEQ ID NO:24)

One μl of PCR product from this reaction was used as template in a second reaction, carried out as described above, with oligonucleotide SEQ ID NO:17 as the 3' oligonucleotide and the following as the 5' oligonucleotide:

CACCCAACCGCTAGCGGTAGTGGTACTG-GCGGTGACGAAGTTGAC (SEQ ID NO:25)

This reaction was designed to add DNA encoding an eight amino acid linker (ASGSGTGG, SEQ ID NO:26), including a 5' NheI site, to the 5' end of the product DNA from the previous reaction. PCR product from the second of the two reactions was precipitated with ethanol, resuspended in water, and digested with NheI and XhoI (New England Biolabs) as described by the manufacturer. This fragment was cloned into a vector digested with the same enzymes and treated with calf intestinal phosphatase in a ligation reaction similar to that described in Example 1. The ligation products were transformed into E. coli GM221 cells according to the procedure described in Example 1. Colonies that resulted from the ligation were screened by the PCR procedure described above for the presence of appropriately-sized insert using oligonucleotides directed against flanking vector sequence. DNA sequence analysis of PCR-positive clones confirmed the addition of DNA beginning with a 5' NheI restriction site that encodes an eight amino acid linker and a four amino acid caspase 3 cleavage site to the 5' end of mature, human GCSF. The sequence of GCSF and the presence of a 3' XhoI site following the stop codon were also confirmed. The NheI to XhoI fragment was removed from the shuttle vector in a restriction digest that followed the manufacturer's instructions (New England Biolabs) and subcloned into the pAMG21UGI vector described in Example 1 in a ligation reaction similar to that used previously. The ligation products were transformed into E. coli GM221 cells according to the procedure described in Example 1 and colonies were screened by PCR for the presence of insert (see Example 1).

Figure 4:
FIG. 4 is an SDS gel which demonstrates that a UGI/GCSF fusion is produced primarily in the soluble fraction when the gene encoding the chimera is expressed in E-coli. Lane 1 is a molecular weight marker. Lane 2 is a GCSF pre-induction lysate sample. Lane 3 is a GCSF whole cell lysate after induction. Lane 4 is a GCSF post-induction, post-centrifugation insoluble fraction. Lane 5 is a GCSF post-induction, post-centrifugation soluble fraction. Lane 6 is a UGI/GCSF pre-induction lysate sample. Lane 7 is a UGI/GCSF whole cell lysate after induction. Lane 8 is the UGI/GCSF post-induction, post-centrifugation insoluble fraction and Lane 9 is the UGI/GCSF post-induction, post-centrifugation soluble fraction. Equal amounts of insoluble and soluble fractions were analyzed.

The expression level and solubility of the UGI/GCSF fusion protein were determined for two of the clones that showed the presence of insert DNA by PCR. Five ml of Luria broth containing 40 μg/ml kanamycin were inoculated with GM221 cells harboring pAMG21 UGI/GCSF. The culture was incubated shaking overnight. Fifty μl of the overnight culture were diluted into 50 ml of Luria broth in a 250 ml shaker flask containing 40 μg/ml kanamycin. The resulting cultures were grown shaking at 30° C. for four to five hours until an optical density at 600 nm close to 0.8 was reached (spectrophotometer model no. DU640, Beckman Instruments, Fullerton, Calif.). At this point a preinduction sample was removed and autoinducer was added to a final concentration of 30 ng/ml. After about four hours of shaking at 30° C., a post-induction sample was taken. The remaining cells were pelleted and stored overnight at −20° C. The following day the cells were resuspended in TE and soluble and insoluble fractions were prepared as described in Example 1. Equal amounts of soluble and insoluble fractions were analyzed by SDS-PAGE, along with the pre- and post-induction samples. Also shown on the gel in FIG. 4 is the expression and solubility of GCSF alone. As can be seen, a band of the size expected for the fusion protein, about 30 kDa, was observed exclusively in the soluble fraction. GCSF expressed without UGI (approximately 20 kDa band) was found exclusively in the insoluble fraction. This result suggests that expression of GCSF as a fusion with UGI greatly enhances solubility.

Figure 5:
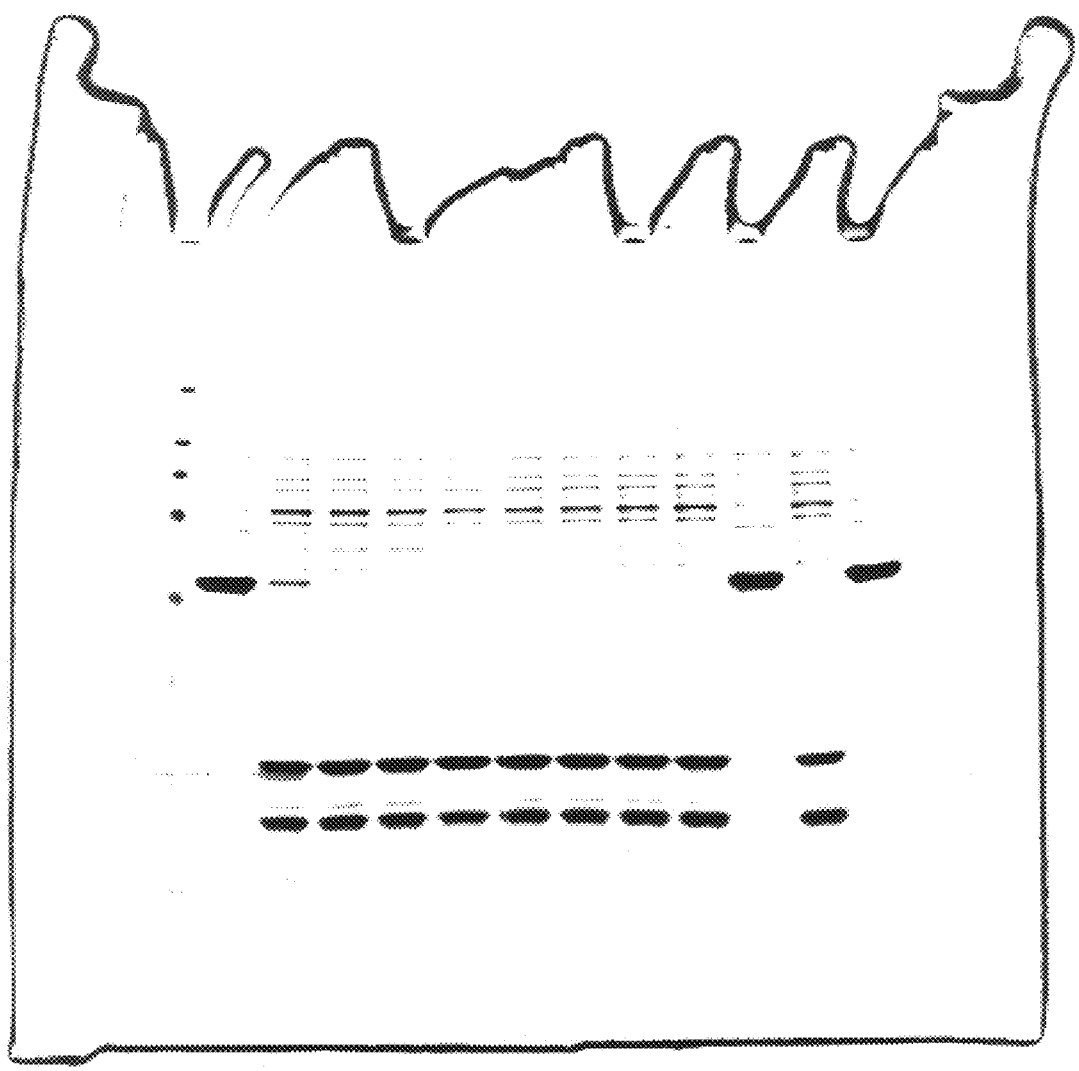
FIG. 5 is an SDS gel which demonstrates that the GCSF portion of the UGI/GCSF fusion produced in E. coli remains soluble after removal of the UGI. Lane 1 is a molecular weight marker. Lane 2 is a UGI/GCSF post-induction, post-centrifugation soluble fraction. Lanes 3–10 are UGI/GCSF post-induction, post-centrifugation soluble fractions which have been incubated in the presence of caspase 3 for various lengths of time (1, 2, 5, 10, 15, 20, 25, and 30 minutes). Lane 11 is a UGI/GCSF post-induction, post-centrifugation soluble fraction incubated 30 minutes without caspase 3. Lane 12 is a UGI/GCSF post-induction, post-centrifugation soluble fraction incubated 30 minutes in the presence of caspase 3 and following a 30 minute centrifugation. Lane 13 is the UGI/GCSF post-induction, post-centrifugation soluble fraction incubated 30 minutes without caspase 3 and following a 30 minute centrifugation. Equal amounts of soluble fractions were analyzed.

To determine whether the GCSF portion of the UGI/GCSF fusion would remain soluble after removal of the UGI, a lysate from a culture expressing the UGI/GCSF fusion prepared as described above was mixed with a lysate from a cell expressing soluble, active caspase 3; Mittl et al., J. Biol. Chem., 272:6539–6547 (1997). 0.4 ml of each lysate were mixed together in a tube on ice. The mixture was then incubated at 37° C. and 50 μl samples were withdrawn at the following times: 1, 2, 5, 10, 15, 20, 25, and 30 minutes. The samples were analyzed by SDS-PAGE. As a control, the fusion lysate was incubated for 30 minutes at 37° C. without addition of the lysate containing caspase 3. Furthermore, both digested and undigested samples, removed after 30 minutes of incubation at 37° C., were centrifuged at 18,000×g for 30 minutes. An aliquot of the supernatant fraction from this centrifugation was analyzed by SDS-PAGE to further demonstrate the solubility of the released GCSF. The gel analysis is shown in FIG. 5. Bands on the gel representing GCSF and UGI are visible at the earliest time tested. After one minute of incubation, cleavage of the fusion is more than 90% complete (lane 3). No cleavage occurs without the addition of caspase 3 (lane 11). Both the GCSF and UGI remain soluble after cleavage (lane 12). These data suggest that fusion of GCSF to UGI allows proper folding of both proteins to occur.

EXAMPLE 3

This example describes the preparation of a UGI/IKK-2 fusion.

A fusion protein containing UGI and the catalytic domain of the kinase IKK2 was prepared as follows. Fragments of DNA encoding the N-terminal region of IKK2, presumed to contain the catalytic domain; Zandi et al., Cell, 91:243–252 (1997), were obtained by standard cloning techniques. A UGI/IKK2 fusion construct, containing an eight amino acid linker (ASGSGTGG, SEQ ID NO:26), a cleavage site for the caspase 3 protease, a seven histidine tag, and a cleavage site for enterokinase protease (DDDDK, SEQ ID NO:27) at the N-terminus of IKK2 was prepared.

Figure 6:
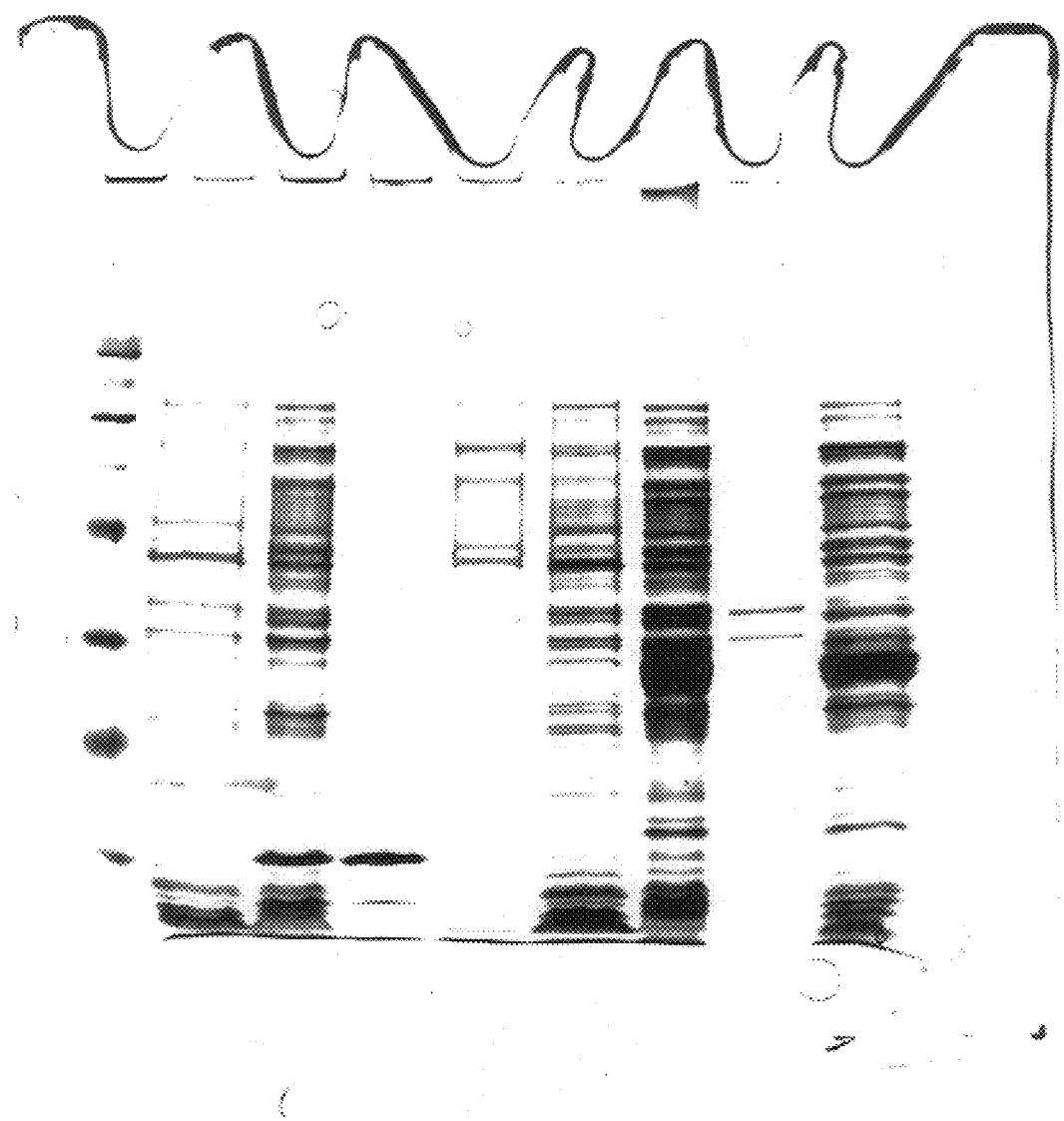
FIG. 6 is an SDS gel which demonstrates that a UGI/IKK2 fusion is expressed primarily in the soluble fraction when expressed in E-coli. Lane 1 is a molecular weight marker. Lane 2 is a IKK2 pre-induction sample. Lane 3 is a IKK2 whole cell lysate after induction. Lane 4 is a IKK2 post-induction, post-centrifugation insoluble fraction and Lane 5 is a IKK2 post-induction, post-centrifugation soluble fraction. Lane 6 is a UGI/IKK2 pre-induction sample. Lane 7 is a UGI/IKK2 whole cell lysate after induction. Lane 8 is a UGI/IKK2 post-induction, post-centrifugation insoluble fraction and Lane 9 is a UGI/IKK2 post-induction, post-centrifugation soluble fraction. Equal amounts of soluble fractions were analyzed.

Expression and solubility of the fusion protein were determined as described in Example 1 (except that 1 ml instead of 50 μl of the overnight culture was diluted into 50 ml Luria broth containing 40 μg/ml kanamycin). FIG. 6 demonstrates that expression of IKK2 as a fusion with UGI greatly enhances solubility. A band of approximately 40 kDa, corresponding to IKK2 alone, is found exclusively in the insoluble fraction (Lane 4). Virtually all of the fusion protein is found in the soluble fraction (Lane 9), visible as a band of about 52 kDa.

Figure 7:
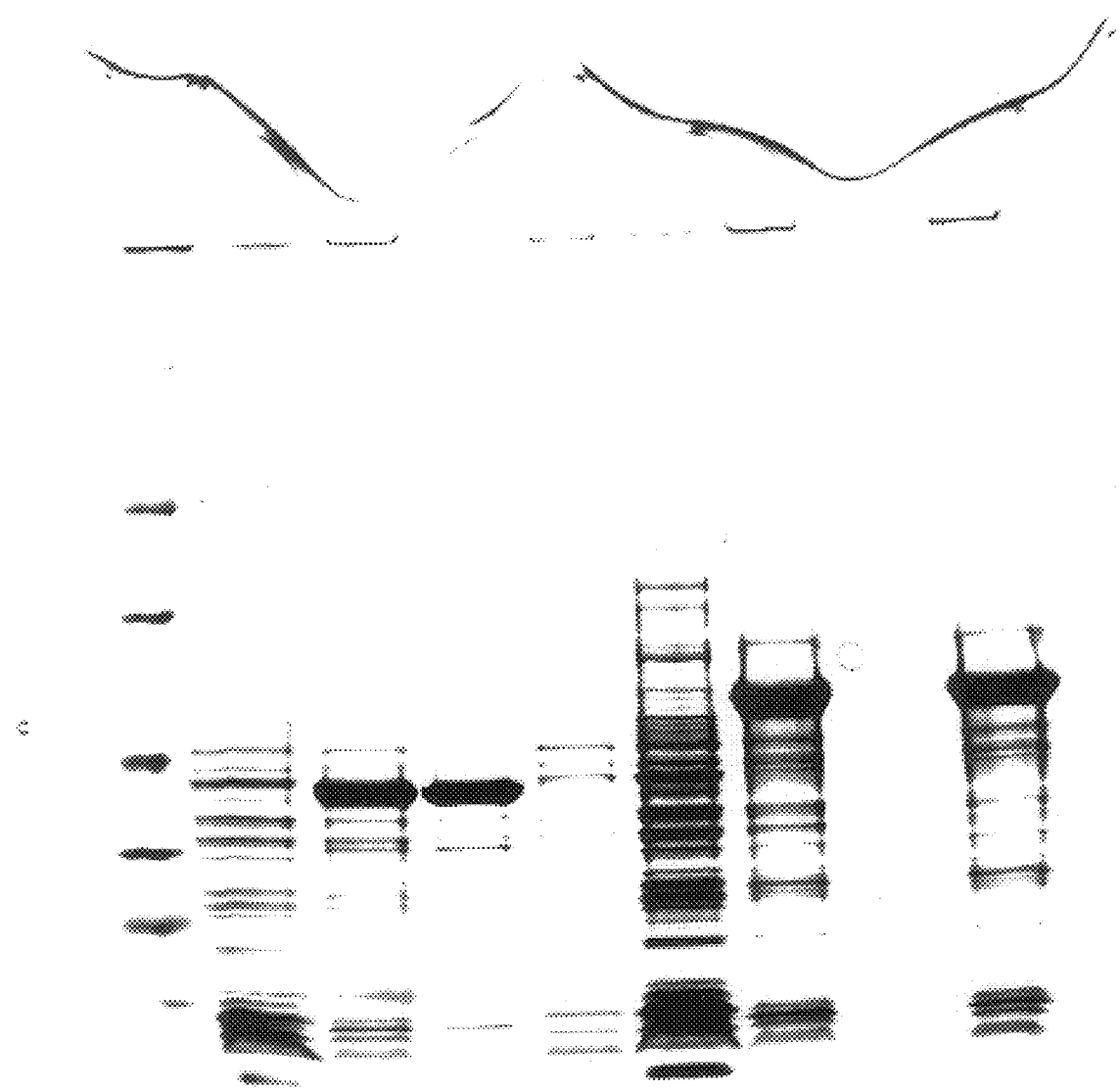
FIG. 7 is an SDS gel which demonstrates that the IKK2 portion of the UGI/IKK2 fusion produced in E. coli remains soluble after removal of the UGI. Lane 1 is a molecular weight marker. Lane 2 is a UGI/IKK2 whole cell lysate after induction. Lane 3 is a UGI/IKK2 post-induction, post-centrifugation insoluble fraction without caspase 3. Lane 4 is a IKK2 post-induction, post-centrifugation soluble fraction without caspase 3. Lane 5 is a UGI/IKK2 post-induction, post-centrifugation insoluble fraction in the presence of caspase 3. Lane 6 is a IKK2 post-induction, post-centrifugation soluble fraction in the presence of caspase 3. Equal amounts of soluble fractions were analyzed.

A lysate from a culture producing the UGI/IKK2 fusion, prepared as described above, was mixed with purified caspase 3 to separate UGI and IKK2. Four μl of purified caspase 3 (about 2 mg/ml) were added to 1 ml of lysate in an Eppendorf tube. The mixture was incubated at room temperature for 2 hours, and then centrifuged for 30 min to separate soluble and insoluble fractions. Aliquots of each fraction were analyzed by SDS PAGE. As can be seen in FIG. 7, no cleavage occurred without addition of caspase 3 (Lanes 2–4). About 95% of IKK2 remained soluble after cleavage (Lane 6). These data suggest that the kinase domain is properly folded while attached to UGI.

EXAMPLE 4

This example describes the preparation of a UGI/OPG ligand fusion.

To prepare a DNA construct for the expression of a UGI/osteoprotegerin ligand fusion protein ("UGI/OPGL"), DNA encoding the extracellular domain of human osteoprotegerin ligand ("OPGL") from amino acid 153 to amino acid 317; Lacey et al., *Cell*, 93:165–176 (1998), was used as a template in a two step PCR procedure. The first PCR reaction was designed to add DNA encoding a cleavage site for the caspase 3 protease to the 5' end of the region coding for OPGL and an XhoI restriction site following a stop codon to the 3' end. The following oligonucleotides were used in a PCR reaction similar to those described above:

GGCGGTGACGAAGTTGACAAACT-
TGAAGCTCAACCT (SEQ ID NO:28)

CACCCAACCCTCGAGTTAATC-
TATATCTCGAACTTT (SEQ ID NO:29)

One µl of PCR product from this reaction was used as template in a second reaction, carried out as described in Example 1, with oligonucleotide SEQ ID NO:21 as the 3' oligonucleotide and oligonucleotide SEQ ID NO:19 as the 5' oligonucleotide. The second reaction added DNA encoding an eight amino acid linker (ASGSGTGG, SEQ ID NO:26), including a 5' NheI site, to the 5' end of the product DNA from the previous reaction. The product of the second PCR reaction was precipitated with ethanol, resuspended in water, and digested with restriction endonucleases NheI and XhoI as described by the manufacturer (New England Biolabs).

Figure 8:
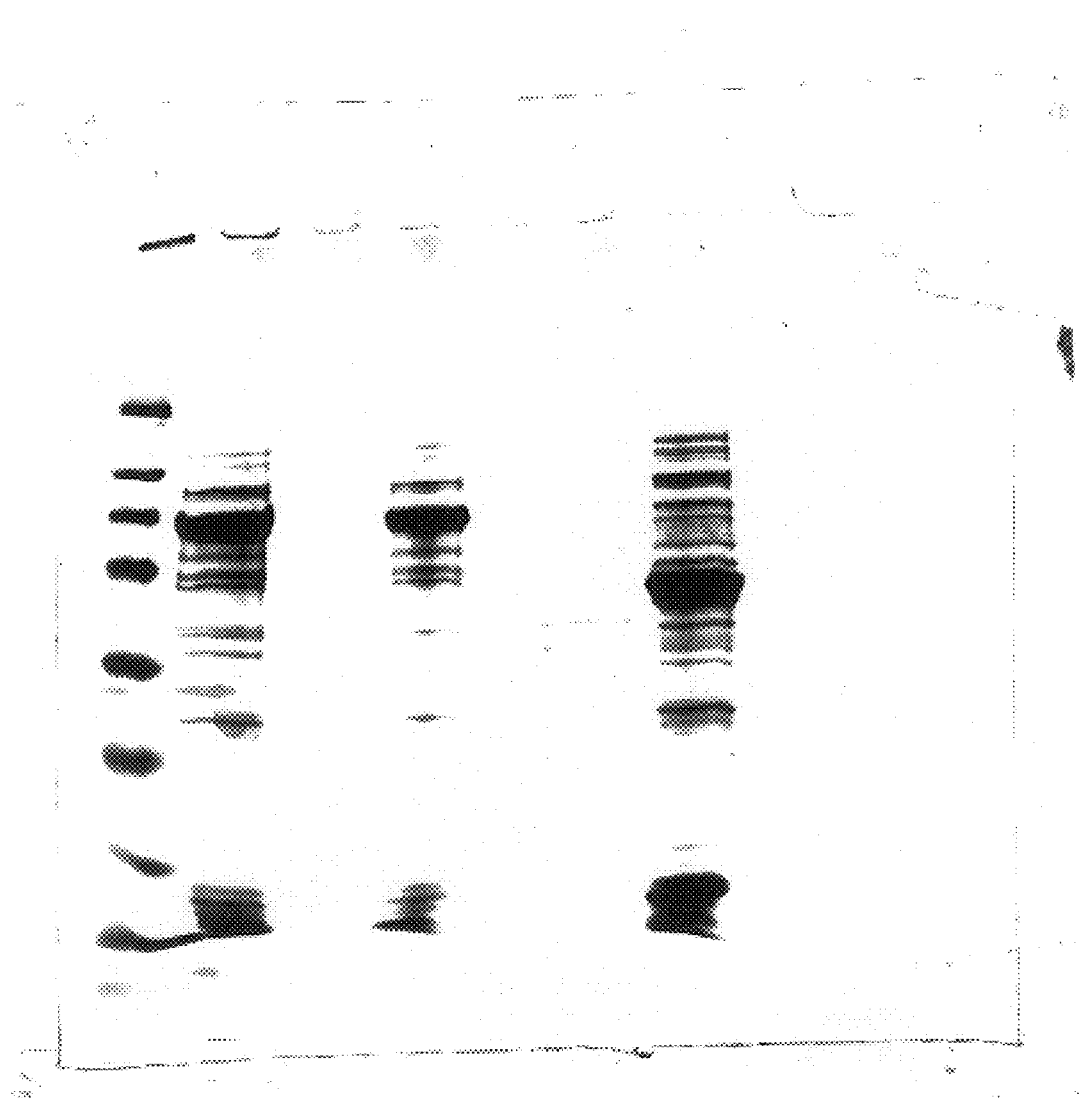
FIG. 8 is an SDS gel which demonstrates that a UGI/OPGL fusion is expressed primarily in the soluble fraction when expressed in E-coli. Lane 1 is a molecular weight marker. Lane 2 is a OPGL pre-induction sample. Lane 3 is a OPGL whole cell lysate after induction. Lane 4 is a OPGL post-induction, post-centrifugation insoluble fraction and Lane 5 is a OPGL post-induction, post-centrifugation soluble fraction. Lane 6 is a UGI/OPGL pre-induction sample. Lane 7 is a UGI/OPGL whole cell lysate after induction. Lane 8 is a UGI/OPGL post-induction, post-centrifugation insoluble fraction and Lane 9 is a UGI/OPGL post-induction, post-centrifugation soluble fraction. Equal amounts of insoluble and soluble fractions were analyzed.

Previous experience fusing OPGL to other partners indicated that production of a soluble OPGL fusion protein is toxic to the bacterial strain GM221. In order to minimize preinduction leakage, the PCR product encoding OPGL was cloned into a vector in which the UGI coding region was preceded by a MS2 site (see Example 1). The vector was digested with NheI and XhoI according to the manufacturer's instructions (New England Biolabs) and treated with calf intestinal phosphatase (Boehringer Mannheim, one unit for 30 minutes at 37° C.). The vector and insert DNAs were mixed in a ligation reaction similar to that described above. The ligation product was transformed by electroporation into an *E. coli* strain that expresses MS2 coat protein (PCT WO 99/38985). Colonies were screened by PCR for the presence of an insert of the correct size using primers that hybridize to the vector sequence outside the cloned region. Positive clones were selected for confirmation by automated DNA sequence analysis. The vector containing the UGI/OPGL fusion construct was transformed into *E. coli* GM221 cells as described in Example 1. One of the resulting clones was selected for expression studies. Expression and solubility of the UGI/OPGL fusion protein were examined as described in Example 1. As can be seen in FIG. 8, OPGL expressed without a fusion partner is almost entirely insoluble (Lanes 2–5). A prominent band of approximately 18 kDa can be seen in the insoluble fraction (Lane 4). However, more than 95% of the fusion protein (approximately 28 kDa) is soluble (Lanes 6–9).

EXAMPLE 5

This example describes the preparation of a UGI/GCSF Receptor ("UGI/GCSFR") fusion.

A construct for the expression of a UGI/GCSFR fusion protein was prepared as follows. A vector containing the extracellular domain of GCSFR; Fukunaga et al., *EMBO J.* 10:2855–2865 (1991) fused to GF14; Wu et al. *Plant Physiol.*, 114:1421–1431 (1997); Lu et al., *The Plant Cell*, 6:501–510 (1993), was digested with NheI and BamHI (New England Biolabs) according to the manufacturer's instructions to yield a DNA fragment coding for a five amino acid linker (ASGTG, SEQ ID NO:30) and GCSFR. This fragment was subcloned into the pAMG21UGI vector described in Example 1. Restriction digests and ligations were performed as described earlier. Ligation products were transformed into *E.coli* GM221 by electroporation and the resulting colonies were screened by PCR for the presence of insert. Two of the clones that were positive by PCR contained the correct DNA sequence, as confirmed by automated DNA sequencing. One of these clones was selected for expression studies.

Figure 9:
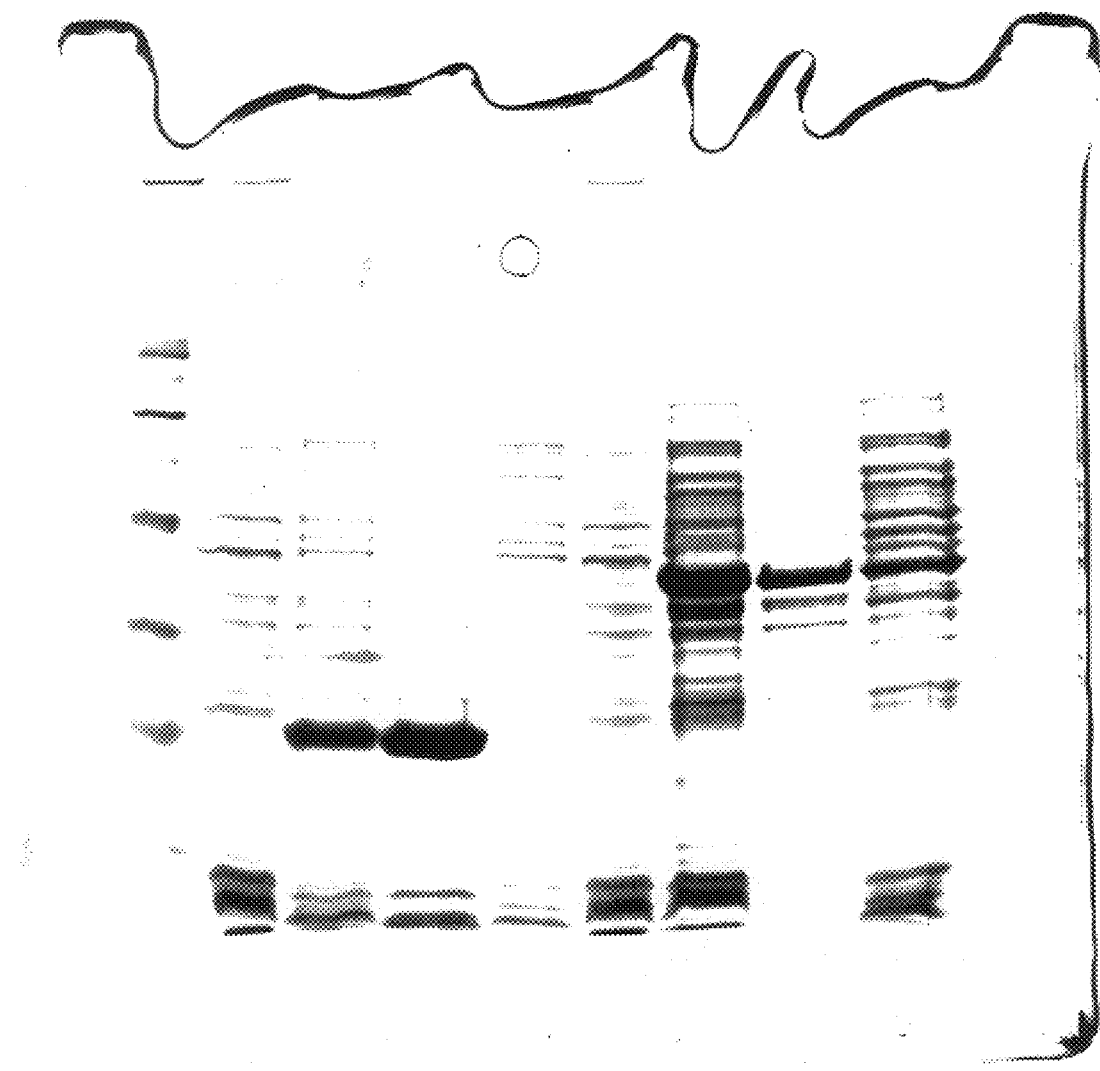
FIG. 9 is an SDS gel which demonstrates that a UGI/GCSFR fusion is found primarily in the soluble fraction when the chimera is produced in E-coli. Lane 1 is a molecular weight marker. Lane 2 is a GCSFR pre-induction sample. Lane 3 is a GCSFR whole cell lysate after induction. Lane 4 is a GCSFR post-induction, post-centrifugation insoluble fraction. Lane 5 is a GCSFR post-induction, post-centrifugation soluble fraction. Lane 6 is a UGI/GCSFR pre-induction sample. Lane 7 is a UGI/GCSFR whole cell lysate after induction. Lane 8 is a UGI/GCSFR post-induction, post-centrifugation insoluble fraction and Lane 9 is a UGI/GCSFR post-induction, post-centrifugation soluble fraction. Equal amounts of insoluble and soluble fractions were analyzed.

Expression and solubility of UGI/GCSFR fusion protein were examined in the same manner as described in Example 1 except that 1 ml, instead of 50 µl, of the overnight culture was diluted into 50 ml Luria broth containing 40 µg/ml kanamycin to grow the cultures used in expression studies. As shown in FIG. 9, all of the GCSFR produced without a fusion partner is insoluble (approximately 23 kDa band in insoluble fraction, Lane 4), while about 40% of the fusion protein is soluble (approximately 33 kDa band, Lane 9).

SEQUENCE LISTING

<160> NUMBER OF SEQ ID NOS: 30

<210> SEQ ID NO 1
<211> LENGTH: 285
<212> TYPE: DNA
<213> ORGANISM: Bacillus subtilis phage PBS2

<400> SEQUENCE: 1

```
atgaaacacc atcaccatca ccatcacaca aatttatctg acatcattga aaaagaaaca      60
ggaaaacaac tagtgattca agaatcaatt ctaatgttac cagaagaagt agaggaagta     120
attgggaata aaccagaaag tgatatttta gttcatactg cttatgatga aagtacagat     180
gaaaatgtaa tgctattaac ttcagatgct ccagaatata aaccttgggc tttagtaatt     240
caagacagta atggagaaaa taaaattaaa atgttagcta gctaa                    285
```

<210> SEQ ID NO 2
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic oligonucleotide designed to
      correspond to a portion of coding sequence of uracil DNA
      glycosylase inhibitor protein from PBS

<400> SEQUENCE: 2
acaaacacca catatgaaac accatcacca tcaccat                               37

<210> SEQ ID NO 3
<211> LENGTH: 40
<212> TYPE: DNA
<213> ORGANISM: Artificial Sequence
<220> FEATURE:
<221> NAME/KEY: misc/feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 3
cacacaaatt tatctgacat cattgaaaaa gaaacaggaa                            40

<210> SEQ ID NO 4
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 4
aacaactagt gattcaagaa tcaattctaa tgttaccaga                            40

<210> SEQ ID NO 5
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 5
agaagtagag gaagtaattg ggaataaacc agaaagtgat                            40

<210> SEQ ID NO 6
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 6
attttagttc atactgctta tgatgagtcg acagatgaaa                  40

<210> SEQ ID NO 7
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 7
atgtaatgct attaacttca gatgctccag aatataaacc                  40

<210> SEQ ID NO 8
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 8 atgggctta gtaattcaag acagtaatgg agaaaataaa                   40

<210> SEQ ID NO 9
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 9
attaaaatgt taggtagtgg tactggcggt gctagctaat                  40

<210> SEQ ID NO 10
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic oligonucleotide designed to
      correspond to a portion of coding sequence of uracil DNA
      glycosylase inhibitor protein from PBS

<400> SEQUENCE: 10
cacccaaccc tcgagattag ctagcaccgc cagta                       35

<210> SEQ ID NO 11
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 11
ccactaccta acattttaat tttatttttct ccattactgt        40

<210> SEQ ID NO 12
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 12
cttgaattac taaagcccat ggtttatatt ctggagcatc        40

<210> SEQ ID NO 13
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 13
tgaagttaat agcattacat tttcatctgt cgactcatca        40

<210> SEQ ID NO 14
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 14
taagcagtat gaactaaaat atcactttct ggtttattcc        40

<210> SEQ ID NO 15
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 15
caattacttc ctctacttct tctggtaaca ttagaattga        40

<210> SEQ ID NO 16
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

```
<400> SEQUENCE: 16
ttcttgaatc actagttgtt ttcctgtttc tttttcaatg                              40

<210> SEQ ID NO 17
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic oligonucleotide designed to
      correspond to a portion of coding sequence of uracil DNA
      glycosylase inhibitor protein from PBS

<400> SEQUENCE: 17
atgtcagata aatttgtgtg atggtgatgg tgatggtgtt                              40

<210> SEQ ID NO 18
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic oligonucleotide designed to repair
      sequence errors in a synthetic uracil DNA glycosylase inhibitor
      protein sequence

<400> SEQUENCE: 18
tcaccatcac cacacaaatt tatctgacat cattg                                   35

<210> SEQ ID NO 19
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic oligonucleotide designed to repair
      sequence errors in a synthetic uracil DNA glycosylase inhibitor
      protein sequence

<400> SEQUENCE: 19
caaacaccac atatgaaaca ccatcatcac catcaccaca c                            41

<210> SEQ ID NO 20
<211> LENGTH: 47
<212> TYPE: DNA
<213> ORGANISM: Artificial Sequence
<220> FEATURE:
<221> NAME/KEY: misc_feature
<222> LOCATION: (1)..(47)
<223> OTHER INFORMATION: Synthetic oligonucleotide designed to remove a
      linker region in a synthetic uracil DNA glycosylase inhibitor
      protein sequence

<400> SEQUENCE: 20
cacccaaacc tcgagttagc tagctaacat tttaatttta ttttctc                      47

<210> SEQ ID NO 21
<211> LENGTH: 53
<212> TYPE: DNA
<213> ORGANISM: Artificial Sequence
<220> FEATURE:
<221> NAME/KEY: misc_feature
<222> LOCATION: (1)..(53)
<223> OTHER INFORMATION: Synthetic oligonucleotide designed to add an
      MS2 site to the 5' end of a synthetic uracil DNA glycosylase
      inhibitor protein sequence
```

<400> SEQUENCE: 21
cacccaacct ctagaaaaca tgaggatcac ccatgacaaa tttatctgac atc    53

<210> SEQ ID NO 22
<211> LENGTH: 4
<212> TYPE: PRT
<213> ORGANISM: caspase 3 protease

<400> SEQUENCE: 22

Asp Glu Val Asp
1

<210> SEQ ID NO 23
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic oligonucleotide designed to add a
      cleavage site for the caspase 3 protease to the 5' end of the
      region coding for human granulocyte colony stimulating factor
      (GCSF)

<400> SEQUENCE: 23
ggcggtgacg aagttgacac tccattaggt cctgc    35

<210> SEQ ID NO 24
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide designed to add a
      restriction site following a stop codon to the 3' end of the
      region coding for human GCS

<400> SEQUENCE: 24
cacccactcg agattacggc tgagccagat g    31

<210> SEQ ID NO 25
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Synthetic oligonucleotide designed to add a
      specific linker to the 5' end of the region coding for human GCS

<400> SEQUENCE: 25
cacccaaccg ctagcggtag tggtactggc ggtgacgaag ttgac    45

<210> SEQ ID NO 26
<211> LENGTH: 8
<212> TYPE: PRT
<213> ORGANISM: Artificial Sequence
<220> FEATURE:
<221> NAME/KEY: misc_feature
<222> LOCATION: (1)..(8)
<223> OTHER INFORMATION: Designed peptide to act as a linker in a fusion
      protein

<400> SEQUENCE: 26

Ala Ser Gly Ser Gly Thr Gly Gly
1               5

```
<210> SEQ ID NO 27
<211> LENGTH: 5
<212> TYPE: PRT
<213> ORGANISM: Artificial Sequence
<220> FEATURE:
<221> NAME/KEY: misc_feature
<222> LOCATION: (1)..(5)
<223> OTHER INFORMATION: Designed peptide to act as a cleavage site for
      enterokinase protease

<400> SEQUENCE: 27

Asp Asp Asp Asp Lys
1               5

<210> SEQ ID NO 28
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic oligonucleotide designed to add DNA
      encoding a cleavage site for the caspase 3 protease to the 5' end
      of the region coding for osteoprotegerin ligand (OPGL)

<400> SEQUENCE: 28
ggcggtgacg aagttgacaa acttgaagct caacct                              36

<210> SEQ ID NO 29
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic oligonucleotide designed to add a
      restriction site to the 3' end of the region coding for OPG

<400> SEQUENCE: 29
cacccaaccc tcgagttaat ctatatctcg aacttt                              36

<210> SEQ ID NO 30
<211> LENGTH: 5
<212> TYPE: PRT
<213> ORGANISM: Artificial Sequence
<220> FEATURE:
<221> NAME/KEY: misc_feature
<222> LOCATION: (1)..(5)
<223> OTHER INFORMATION: Designed peptide to act as a linker in a fusion
      protein

<400> SEQUENCE: 30

Ala Ser Gly Thr Gly
1               5
```

What is claimed is:

1. A method of increasing the solubility of a protein of interest produced in a host cell comprising expressing the protein as a fusion protein with Uracil DNA glycosylase inhibitor (UGI).

2. The method of claim 1 wherein the protein of interest is selected from the group consisting of: extracellular domains of membrane-bound receptor proteins, cytokines and cytokine-like proteins, kinase domains of serine/threonine kinases, and members of the TNF family.

3. The method of claim 1 wherein the host cell is a prokaryotic cell.

4. The method of claim 3 wherein the host cell is an *E. coli* cell.

5. The method of claim 1 wherein the UGI is encoded by the nucleic acid molecule of SEQ ID NO:1.

6. The method of claim 1 wherein the fusion protein contains a linker peptide.

7. The method of claim 6 wherein the protein of interest is selected from the group consisting of: extracellular domains of membrane-bound receptor proteins, cytokines and cytokine-like proteins, kinase domains of serine/threonine kinases, and members of the TNF family.

8. The method of claim 6 wherein the host cell is a prokaryotic cell.

9. The method of claim 8 wherein the host cell is an *E. coli* cell.

* * * * *

UNITED STATES PATENT AND TRADEMARK OFFICE
CERTIFICATE OF CORRECTION

PATENT NO.      : 6,632,638 B1
DATED           : October 14, 2003
INVENTOR(S)     : M. Snavely et al.

It is certified that error appears in the above-identified patent and that said Letters Patent is hereby corrected as shown below:

<u>Column 12,</u>
Lines 42 and 45, change "DNTP" to -- dNTP --.
Line 64, change "UFD" to -- uFD --.

<u>Column 14,</u>
Line 14, change "10M" to -- 10mM --.

Signed and Sealed this

Eighteenth Day of May, 2004

JON W. DUDAS
*Acting Director of the United States Patent and Trademark Office*